(12) United States Patent
Oliveira et al.

(10) Patent No.: US 8,988,074 B2
(45) Date of Patent: Mar. 24, 2015

(54) METHOD FOR GENERATING MR IMAGES AND CORRESPONDINGLY EMBODIED MAGNETIC RESONANCE SCANNER

(75) Inventors: Andre De Oliveira, Erlangen (DE); Matthias Fenchel, Erlangen (DE); Wilhelm Horger, Schwaig (DE)

(73) Assignee: Siemens Aktiengesellschaft, Munich (DE)

( * ) Notice: Subject to any disclaimer, the term of this patent is extended or adjusted under 35 U.S.C. 154(b) by 226 days.

(21) Appl. No.: 13/176,010

(22) Filed: Jul. 5, 2011

(65) Prior Publication Data

US 2012/0010495 A1  Jan. 12, 2012

(30) Foreign Application Priority Data

Jul. 7, 2010  (DE) .......................... 10 2010 026 376

(51) Int. Cl.
| G01V 3/00 | (2006.01) |
| G01R 33/56 | (2006.01) |
| A61B 5/055 | (2006.01) |
| G01R 33/54 | (2006.01) |
| A61B 5/20 | (2006.01) |
| A61B 5/00 | (2006.01) |

(52) U.S. Cl.
CPC ............ *G01R 33/5608* (2013.01); *A61B 5/055* (2013.01); *G01R 33/543* (2013.01); *A61B 5/201* (2013.01); *A61B 5/4064* (2013.01); *A61B 5/4244* (2013.01); *A61B 5/4381* (2013.01)
USPC ......................................... 324/312; 382/128

(58) Field of Classification Search
CPC .................................................. G01R 33/5608
USPC .......... 382/128, 131; 324/312, 306, 307, 309, 324/300
See application file for complete search history.

(56) References Cited

U.S. PATENT DOCUMENTS

| 6,249,595 B1 * | 6/2001 | Foxall et al. ................... 382/128 |
| 6,265,874 B1 * | 7/2001 | McGee et al. ................. 324/312 |
| 7,421,140 B2 * | 9/2008 | Rottem ......................... 382/254 |
| 8,270,695 B2 * | 9/2012 | Luo et al. ....................... 382/128 |
| 2003/0065732 A1 | 4/2003 | Gortler et al. |
| 2008/0279432 A1 | 11/2008 | Assmann et al. |

(Continued)

FOREIGN PATENT DOCUMENTS

| CN | 101034153 A | 9/2007 |
| DE | 10144931 A1 | 4/2003 |
| DE | 102006011253 A1 | 9/2007 |

(Continued)

OTHER PUBLICATIONS

Certified Priority document for German Application No. 10 2010 026 376.1 filed Jul. 7, 2010.

(Continued)

*Primary Examiner* — Louis Arana
(74) *Attorney, Agent, or Firm* — Harness, Dickey & Pierce

(57) ABSTRACT

An embodiment of the invention relates to the generation of MR images of a volume section within an examination object by way of a magnetic resonance scanner. In at least one embodiment, the following steps are performed: generating at least one of the MR images; automatically performing a number of quality inspections on the at least one MR image; and, should one of these quality inspections fail, an action is automatically performed in order to improve a quality when generating more of the MR images.

9 Claims, 3 Drawing Sheets

(56) References Cited

U.S. PATENT DOCUMENTS

2010/0004909 A1 1/2010 Nitz
2011/0153255 A1 6/2011 De Oliveira

FOREIGN PATENT DOCUMENTS

DE 102007022087 A1 11/2008
DE 102007043445 A1 4/2009
DE 102008032007 A1 2/2010
WO WO 2009/034115 3/2009

OTHER PUBLICATIONS

Gedamu Elias, Automated Quality Control of Brain MR Images Montreal Neurological Institute, McGill University, 3801 University Street, Montreal, Quebec, Canada Received Aug. 9, 2007; DOI 10.1002/jmri.21434 2008 Wiley-Liss, Inc.; Others; 2007.

G. Fagiolo, et al: QA Box: Automatic real-time MR Image Quality Assurance system for Clinical Trials Proc. Intl. Soc. Mag. Reson. Med. 15 (2007); Others; 2007.

Chien-Chuan Chen et al: "Quality Assurance of Clinical MRI Scanners Using ACR MRI Phantom: Preliminary Results" Journal of Digital Imaging, vol. 17, No. 4 (Dec.), 2004, pp. 279-284; Others; 2004.

Mortamet B. et al; "Automatic Quality Assessment in Structural Brain Magnetic Resonance Imaging"; Magnetic Resonance in Medicine; vol. 62; pp. 365-372; 2009.

German Office Action mailed Jul. 6, 2013.

* cited by examiner a)   b)   c)

METHOD FOR GENERATING MR IMAGES AND CORRESPONDINGLY EMBODIED MAGNETIC RESONANCE SCANNER

PRIORITY STATEMENT

The present application hereby claims priority under 35 U.S.C. §119 on German patent application number DE 10 2010 026 376.1 filed Jul. 7, 2010, the entire contents of which are hereby incorporated herein by reference.

FIELD

At least one embodiment of the present invention generally relates to a method for generating MR images, which are generated by way of a magnetic resonance scanner and which have a high quality. Moreover, a correspondingly embodied magnetic resonance scanner as well as a corresponding computer program product and a corresponding electronically readable data medium are also described.

BACKGROUND

According to the prior art, the image quality of MR images generated within the scope of an examination of a patient by way of a magnetic resonance scanner is inspected manually after the examination and appropriate modifications are subsequently undertaken if the image quality lies below an acceptable level. These modifications firstly comprise modifications in a protocol, in which appropriate parameters for acquiring the MR images are prescribed, and secondly comprise modifications in respect of the strategy (measurement method) by which the MR images are acquired. However, manual inspecting the MR image quality by an appropriately trained operator (e.g. a medical practitioner or a medical-technical assistant) can lead to an incorrect result, for example if not all of the MR images are inspected or if the operator does not have sufficient experience. Thus the entire examination often has to be repeated by way of the magnetic resonance scanner as a result of low-quality MR images, which leads to additional risks for the patient (contrast agents can lead to e.g. renal fibrosis) and, of course, to additional costs as a result of the repeated use of the expensive magnetic resonance scanner.

A further disadvantage lies in the fact that the manual quality inspection takes a certain amount of time, during which the MR images have to be observed and evaluated. The patient often remains in the magnetic resonance scanner during this time, because a decision in respect of the further procedure, e.g. recording further MR images, can only be made once the quality inspection has been completed. Reference is made to the fact that this period of waiting in the magnetic resonance scanner disadvantageously also occurs if the quality inspection yields a positive result.

SUMMARY

At least one embodiment of the present invention is directed to optimizing the generation of MR images in respect of their generation duration and in respect of their quality.

At least one embodiment of the invention is direct to a method is disclosed for generating MR images, a magnetic resonance scanner, a computer program product and an electronically readable data medium. The dependent claims define preferred and advantageous embodiments of the present invention.

Within the scope of at least one embodiment of the present invention, provision is made for a method for generating MR images of a predetermined volume section within an examination object (more particularly a patient) by way of a magnetic resonance scanner. In the process, the method comprises the following steps:

generating one or more MR images, automatically performing a number of quality inspections on the MR image(s) generated in the above-described step, should one of these quality inspections fail, an action is automatically performed in order to improve an image quality of further MR images that are subsequently recorded by the magnetic resonance scanner, after the action.

Here, the action that is performed automatically in order to improve the image quality of subsequently recorded MR images is understood to mean one or more automatically undertaken interventions, by which parameters or procedures are modified during the generation of the further MR images such that the image quality of the further MR images is better than the image quality of the initially generated MR images.

Compared to the quality inspections being performed manually, automatically performing quality inspections itself advantageously shortens the wait time of the patient in the magnetic resonance scanner. By way of example, the time until a decision is made in respect of performing more examinations by way of the magnetic resonance scanner, dependent on the quality inspections, is shortened. Moreover, the automatically performed actions for improving the image quality (in the case that the initially generated MR images have a low image quality) improve the quality of the finally generated MR images and the risk that occurs in the case of an unnecessary repetition of the examination by way of the magnetic resonance scanner is advantageously at least reduced.

The action performed in order to improve the quality of the MR images generated after this action is dependent on the results of the performed quality inspections in particular (particularly on the result and type of the failed quality inspections).

As a result, the automatically performed action can lead to the failed quality inspections in particular having a better result in the MR images recorded after the action.

At least some of the performed quality inspections can be prescribed dependent on a type of the predetermined volume section.

By way of example, different quality inspections can be used in the case of an MR examination of the liver (as predetermined volume section) than in the case of an MR examination of the prostate or the brain (as predetermined volume section). As a result of matching the quality inspections to the type of the predetermined volume section, the quality of the MR images generated according to at least one embodiment of the invention can advantageously be optimized in respect of this type. Moreover, according to at least one embodiment of the invention it is possible to prescribe that in the case of an abdominal MR examination only the image quality of the kidneys or the liver plays a role and hence only this should be examined.

According to an example embodiment according to the invention, the action or actions that should be performed if a respective quality, inspection fails is prescribed for each of the performed quality inspections.

Hence, according to an example embodiment of the invention, it is not only prescribed which quality inspections are performed but it also possible to configure what action or what actions are automatically performed in the case of a corresponding result of the respective quality inspection.

A protocol that defines parameters and measurement methods for generating the MR images is often generated. The quality inspections can then be configured or determined automatically depending on this protocol.

According to at least one embodiment of the invention, this thereby ensures that the quality inspections are matched to the respectively utilized protocol for generating the MR images in order thus to optimize the image quality of the MR images generated as per this protocol.

In the following text, examples are described for one of the quality inspections, automatically performed according to at least one embodiment of the invention.

Quality inspection as to whether the global signal-to-noise ratio of the MR image to be inspected lies above a first threshold.

To this end, a simple segmentation algorithm is used to segment or localize the body of the patient within the MR image to be inspected. The strength of the measurement signals from the region of the body is subsequently compared to the strength of the signals from outside of the body (from the air). If this ratio lies below the first configurable threshold (e.g. 4), this quality inspection has failed.

Quality inspection as to whether the local signal-to-noise ratio in respect of a predetermined region within the predetermined volume section lies above a second threshold.

To this end, a segmentation algorithm is once again used to segment or localize a predetermined region (for example an organ such as the liver or the kidneys) within the body of the patient. The strength of the measurement signals from this region (organ) is subsequently compared to the strength of the signals from outside of the patient's body (from the air). If this ratio lies below the second configurable threshold, this quality inspection has failed.

Quality inspection as to whether a registered movement of a predetermined region lies above a third threshold during the generation of the MR images.

This quality inspection registers a movement of the patient, which leads to a negative reaction on the image quality of the generated MR images. To this end, e.g. the predetermined region (for example an organ such as the liver) can be segmented by way of a segmentation algorithm. The thickness (dimensions) of the delimitation between the liver and the remaining MR image can then be considered a measure for the movement of the patient. As the delimitation becomes stronger (thicker) the more of a negative impact the movement of the patient has had on the image quality of the respective MR image. Accordingly, this quality inspection registers an (unwanted) movement of the predetermined region and inspects whether this movement is too great.

Quality inspection as to whether aliasing occurs within the MR image to be inspected to an extent that is above a fourth threshold.

An option for registering aliasing or ghost artifacts is to inspect the phase of each row (column) in k-space in respect of whether the MR echo in each case occurs in the center. If this is not the case there is aliasing. Another idea for registering aliasing is to calculate a cross correlation between the respective MR image to be examined and an existing MR image (e.g. an already generated MR image in a neighboring slice). If the result of this cross correlation has a number of peaks (local maxima) the existing image repeats, which indicates aliasing.

Quality inspection as to whether a measurement signal generated by fat has a value that lies above a fifth threshold.

In order to perform this quality inspection, it is possible, for example, to compare an MR image that was generated without fat saturation to the MR image to be inspected with fat saturation. If the measurement signal from the fat in the MR image to be inspected is higher than a predetermined threshold, this quality inspection counts as failed.

Quality inspection, during which the MR image to be inspected is compared to predefined MR images, for example by way of a cross correlation. Only if the results of this cross correlation lie within a predetermined bandwidth does this quality inspection count as passed. This quality inspection can automatically be improved evermore by way of machine learning. To this end, classification methods that classify the MR images to be inspected as acceptable or not acceptable can for example be learned with the aid of algorithms for machine learning.

In respect of this quality inspection, the operator can define a number of (training) MR images and train the method according to the invention on the basis of these MR images such that the method automatically recognizes if the quality of the MR images generated according to at least one embodiment of the invention is less than the quality of the prescribed or defined MR images.

Quality inspection, in which an inspection is performed as to whether setting parameters for generating the MR images lie within predetermined regions.

In this protocol inspection, an inspection is automatically performed as to whether the protocol parameters lie within a specific region that can be configured by the user.

In the following text, actions are described that are performed automatically in the case of one of the quality inspections failing.

One or more setting parameters for generating the MR images are automatically modified, depending on the failed quality inspection or quality inspections, such that an image quality of those MR images that are subsequently generated with the modified setting parameters is improved compared to the image quality of the MR image in which the quality inspection failed.

By way of example, to this end it is possible to configure which conditions should be met by the protocol. Examples for these conditions include:

The duration for performing the protocol should be shorter than a period of time during which the patient can hold his/her breath.

The field of view should be greater than the body of the patient.

Moreover, certain protocol modifications or setting modifications can be configured depending on these conditions. Examples of these protocol modifications include:

A stepwise increase in the repetition time up to a certain value as long as a certain condition is false.

An increase in the field of view (FOV) until the field of view is larger than the body of the patient.

Here, the protocols are modified until all the conditions specified in advance are satisfied. This ensures that the setting parameters that were modified as a result of the failed quality inspection satisfy the respectively configured or prescribed conditions in order thereby also to increase the image quality of the MR images recorded with these modified setting parameters.

A further possible action is that the number of protocols from which one protocol can be selected is restricted such that the protocols of the restricted number improve the quality of those MR images that are produced by one protocol of this number compared to a quality of the MR images generated in advance, in which the quality inspection failed.

In other words, the number of protocols that can be performed is restricted depending on the failed quality inspection such that every protocol in this restricted number increases the image quality. In other words, after this action it is advantageously no longer possible to select a protocol that does not lead to an improvement in the image quality.

This further possible action is described in the following text in an example fashion:

It is assumed that in order to operate the magnetic resonance scanner the operator can normally choose between five measurement protocols, which each have a measurement time (recording time for the MR images) of up to 20 s. By way of example, if it is now the quality inspection that registers an unwanted movement of the patient during the generation of the MR images that fails, the number of protocols that can be performed can automatically be restricted depending on the failed quality inspection such that the operator for example now only has three protocols available for selection, which each only have a measuring time of up to 10 s. With this there advantageously is an automatic reaction to the failure of the corresponding quality inspection and therefore it is only a so-called uncooperative strategy that is pursued, in which the patient may behave uncooperatively and only needs to remain still for 10 s.

Another possible action is for a warning to be generated for the operator of the magnetic resonance scanner.

This optical or acoustic warning informs the operator that the quality inspection failed, and optionally also informs the operator in respect of which quality inspection failed. The operator can then either inspect itself which property of the corresponding MR image is infringing the quality criteria, or the warning already contains this information.

As per a further embodiment of the method according to at least one embodiment of the invention, after a quality inspection has failed, the operator is guided through the modification of the setting parameters or the modification of the strategy. This guiding ensures that the modification in the setting parameters or the strategy leads to the quality of those MR images that are generated after this modification being improved over a quality of that MR image in which the quality inspection failed.

A magnetic resonance scanner for generating MR images of a predetermined volume section in an examination object is also provided within the scope of at least one embodiment of the present invention. Here, the magnetic resonance scanner comprises a basic field magnet, a gradient field system, an RF antenna, and a control apparatus for actuating the gradient field system and the RF antenna, for receiving measurement signals recorded by the RF antenna and for evaluating the measurement signals and for generating the MR images. The magnetic resonance scanner generates one or more MR images and performs a number of quality inspections in respect of each of these MR images. If one of these quality inspections fails, the magnetic resonance scanner performs an action in order thereby to improve an image quality of further MR images that are subsequently generated by the magnetic resonance scanner.

Here, the advantages of the magnetic resonance scanner according to at least one embodiment of the invention substantially correspond to the advantages of the method according to at least one embodiment of the invention, which were explained in detail above, and so repetition is dispensed with here.

Moreover, at least one embodiment of the present invention describes a computer program product, more particularly a computer program or software, that can be loaded into a storage medium of a programmable control or a computational unit of a magnetic resonance scanner. This computer program product can execute all or different embodiments of the method according to the invention described above when the computer program product runs in the control or control apparatus of the magnetic resonance scanner. In the process, the computer program product may require program segments, e.g. libraries and auxiliary functions, for implementing the corresponding embodiments of the methods. In other words, the embodiment directed to the computer program product should more particularly protect a computer program of software that can be used to execute one of the above-described embodiments of the method according to the invention, or that executes said embodiment. Here, the software may be a source code (e.g. in C++) that must still be compiled (translated) and linked or that only has to be interpreted, or an executable software code that only needs to be loaded into the corresponding computational unit for the purpose of execution.

Finally, at least one embodiment of the present invention discloses an electronically readable data medium, e.g. a DVD, a magnetic tape, or a USB stick, on which electronically readable control information, more particularly software (cf. above), is stored. When this control information (software) is read from the data medium and stored in a control or computational unit of a magnetic resonance scanner, it is possible to execute all embodiments according to the invention of the method described above.

At least one embodiment of the present invention is particularly suitable for generating MR images with a predetermined image quality. It goes without saying that at least one embodiment of the present invention is not restricted to this preferred field of application because at least one embodiment of the present invention can also be used for MR spectroscopy in order to generate results in the process with a predetermined quality.

BRIEF DESCRIPTION OF THE DRAWINGS

In the following text, the present invention will be described in detail on the basis of example embodiments with reference to the figures.

DETAILED DESCRIPTION OF THE EXAMPLE EMBODIMENTS

Figure 1:
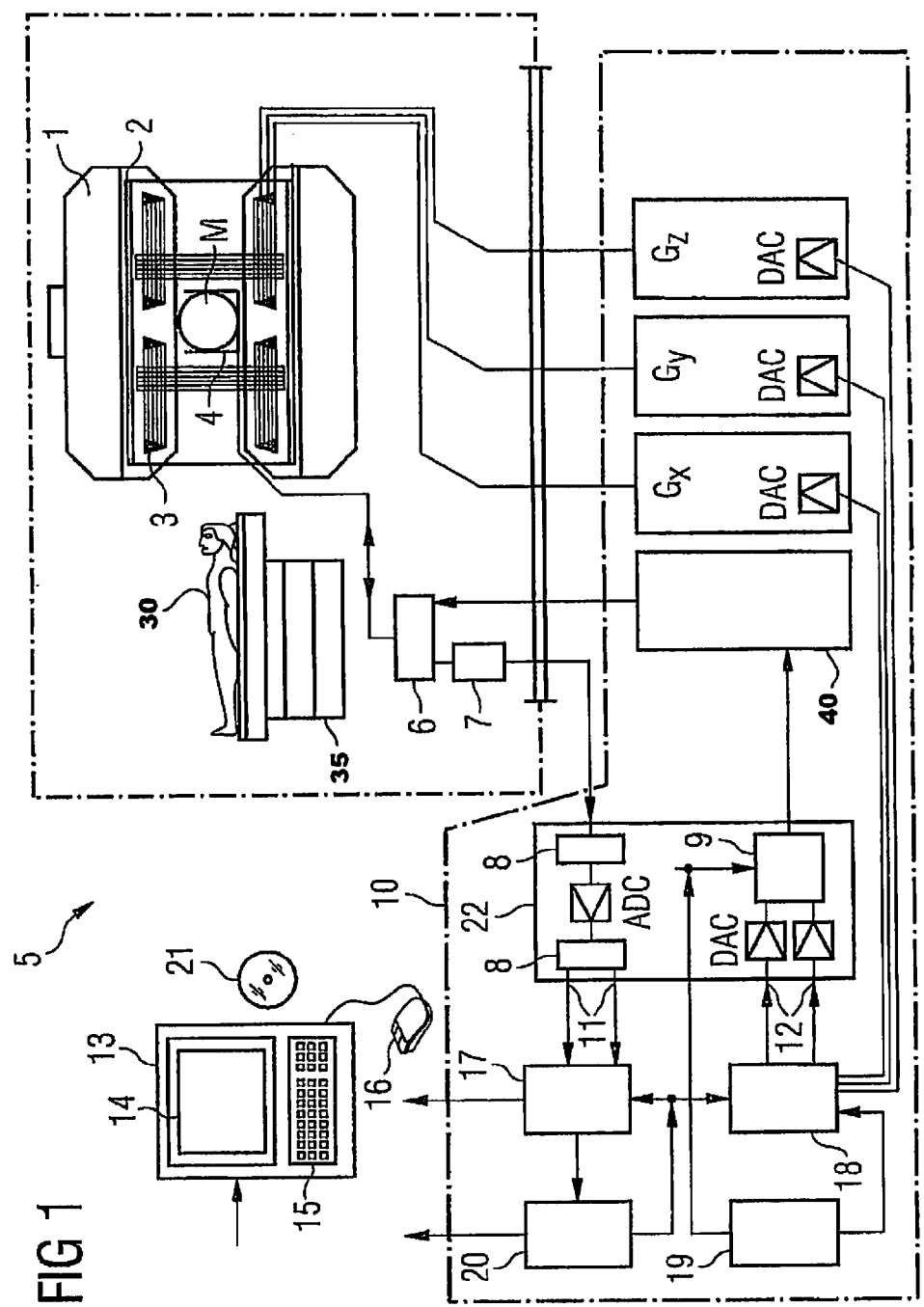
FIG. 1 schematically shows a magnetic resonance scanner according to an embodiment of the invention.

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic illustration of a magnetic resonance scanner 5 (a magnetic resonance imaging scanner or a nuclear magnetic resonance machine). In the process, a basic field magnet 1 generates a strong magnetic field, constant in time, for polarizing or aligning the nuclear spins in an examination region of an object, such as e.g. part of a human body 30 to be examined. The human body 30, as shown in FIG. 1, may be positioned on a bed 35. The high degree of homogeneity of the basic magnetic field required for nuclear magnetic resonance measurements is defined within a typically spherical measurement volume M, into which the parts of the human body 30 to be examined are introduced. In order to support the requirements with respect to homogeneity and more particularly to eliminate time-invariable influences, so-called shim sheets made of ferromagnetic material are attached at suitable locations. Time-varying influences are eliminated by shim coils 2.

A cylindrical gradient coil system 3 is inserted into the basic field magnet 1, the former consisting of three part windings. An amplifier supplies each part winding with current for generating a linear gradient field in the respective direction of the Cartesian coordinate system. The first part winding of the gradient field system 3 generates here a gradient $G_x$ in the x-direction, the second part windings generate a gradient $G_y$ in the y-direction, and the third part winding generates a gradient $G_z$ in the z-direction. The amplifier comprises a digital/analog converter, which is actuated by a sequential control 18 for generating gradient pulses at the right time.

Within the gradient field system 3, there is a radiofrequency antenna 4, which converts the radiofrequency pulses, emitted by a radiofrequency high-power amplifier 40, into an alternating magnetic field for exciting the nuclei and aligning the nuclear spins of the object to be examined or the region to be examined in the object. The radiofrequency antenna 4 consists of one or more RF transmission coils and a plurality of RF reception coils in the form of an annular, preferably linear or matrix-shaped arrangement of component coils. The RF reception coils of the radiofrequency antenna 4 also convert the alternating field emanating from the precessing nuclear spins, i.e. generally the nuclear spin echo signals caused by a pulse frequency from one or more radiofrequency pulses and one or more gradient pulses, into a voltage (measurement signal), which is supplied to a radiofrequency reception channel 8 of a radiofrequency system 22 via an amplifier 7. The radiofrequency system 22 furthermore comprises a transmission channel 9, in which the radiofrequency pulses for exciting the nuclear magnetic resonance are generated. In the process, the respective radiofrequency pulses are represented digitally as a sequence of complex numbers in the sequential control 18 due to a pulse frequency prescribed by the system computer 20. This sequence of numbers is supplied as a real and imaginary part, respectively via one input 12, to a digital/analog converter in the radiofrequency system 22 and from the latter it is supplied to a transmission channel 9. In the transmission channel 9, the pulse sequences are modulated onto a radiofrequency carrier signal, the base frequency of which corresponds to the resonant frequency of the nuclear spins in the measurement volume.

Switching from transmission to reception operation is brought about via a transmission-reception switch 6. The RF transmission coil of the radiofrequency antenna 4 emits the radiofrequency pulses for exciting the nuclear spins into the measurement volume M and samples the resulting echo signals via the RF reception coils. The correspondingly obtained nuclear magnetic resonance signals are demodulated in the reception channel 8' (first demodulator) of the radiofrequency system 22 to an intermediate frequency in a phase-sensitive fashion and are digitized in the analog/digital converter (ADC). This signal is still demodulated to the frequency 0. Demodulation to the frequency 0 and separation into real and imaginary part takes place, after digitization, in a second demodulator 8 in the digital domain. An MR image is reconstructed by an image computer 17 from the measurement data obtained thus.

The measurement data, the image data and the control programs are managed by the system computer 20. On the basis of a prescription with control programs, the sequential control 18 controls the generation of respectively desired pulse frequencies and the corresponding sampling of k-space. More particularly, the sequential control 18 in the process controls the timely switching of the gradients, the emission of radiofrequency pulses with a defined phase amplitude and the reception of the nuclear magnetic resonance signals. The time base for the radiofrequency system 22 and the sequential control 18 is provided by a synthesizer 19. The selection of corresponding control programs for generating an MR image and the display of the generated MR image is brought about via a terminal 13, which comprises a keyboard 15, a mouse 16 and a monitor 14.

Figure 2:
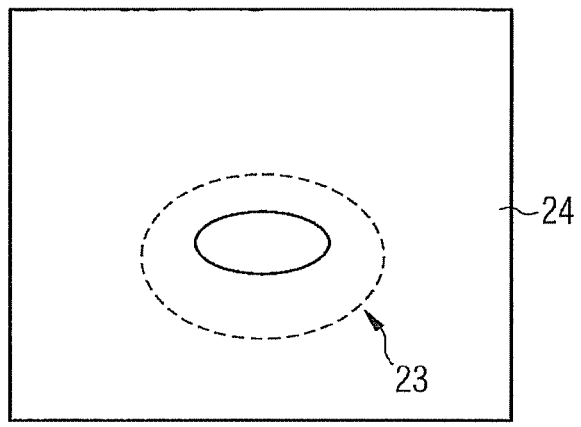
FIG. 2 schematically illustrates a segmented body that is surrounded by air.

FIG. 2 schematically illustrates a segmented body 23 of a patient surrounded by air 24 in an MR image. The global signal-to-noise ratio corresponds to the ratio of the mean strength of the measurement signals from the segmented body 23 to the mean strength of the measurement signals from the surrounding air 24. As per one quality inspection according to the invention, the global signal-to-noise ratio in an MR image to be inspected should lie above a predetermined threshold.

Figure 3:
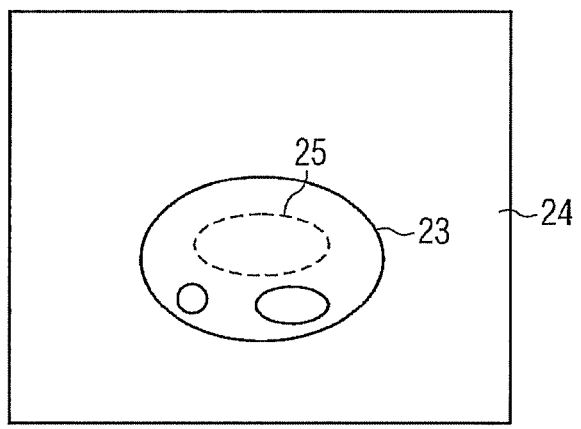
FIG. 3 schematically illustrates a segmented organ within a body that is surrounded by air.

FIG. 3 schematically illustrates a segmented organ (in this case the liver 25) within a segmented body 23 surrounded by air 24. The local signal-to-noise ratio corresponds to the ratio of the mean strength of the measurement signals from the segmented liver 25 to the mean strength of the measurement signals from the surrounding air 24. As per one quality inspection according to the invention, the local signal-to-noise ratio for an MR image to be inspected should lie above a predetermined threshold.

Figure 4:
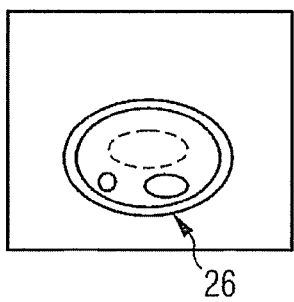
FIG. 4 schematically illustrates MR images without, with good and with poor fat saturation.
Figure 4:
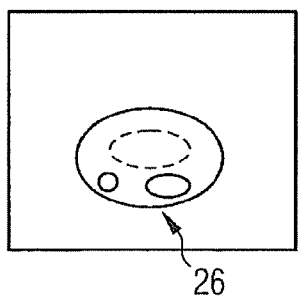
Figure 4:
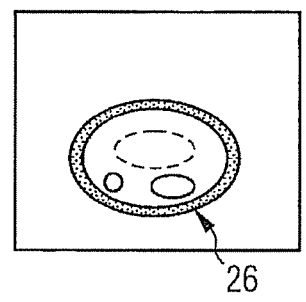

FIG. 4a schematically illustrates an MR image without fat saturation, while FIG. 4b illustrates the corresponding MR image with good fat saturation and FIG. 4c illustrates the corresponding MR image with poor fat saturation. Fat signals 26 caused by the fatty tissue of the patient appear whitish in the respective MR image. While a whitish layer 26 is clearly visible around the body of the patient in FIG. 4a, this layer 26 cannot be identified in FIG. 4b. As a result of the poor fat saturation, the layer 26 in FIG. 4c can by contrast be identified as a gray-white layer. As per one quality inspection, the value of the measurement signals from the fat layer 26 should lie below a threshold, which would be the case in FIG. 4b and would not be the case in FIG. 4c.

Figure 5:
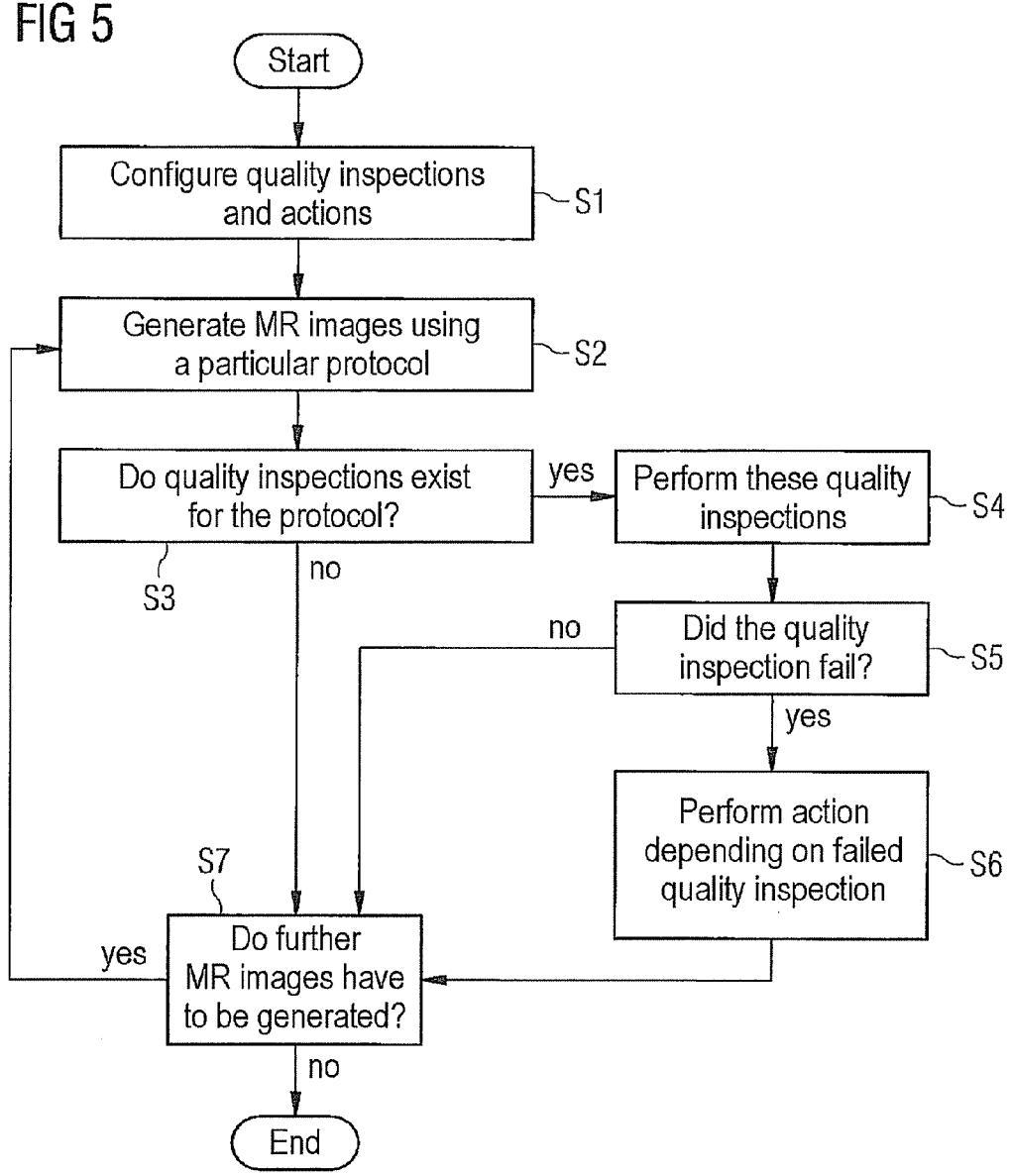
FIG. 5 illustrates a program flowchart of a method according to an embodiment of the invention.

FIG. 5 illustrates a flowchart of an embodiment according to an embodiment of the invention.

Quality inspections and actions that are respectively performed automatically should one of these quality inspections fail are configured in a first step S1.

MR images are illustrated in step S2 on the basis of a protocol determined in advance, which prescribes the performed measurement method and corresponding parameters for this measurement method.

A check is performed in step S3 as to whether quality inspections are defined for the protocol utilized in step S2. Should this not be the case, the method according to an embodiment of the invention branches to step S7, in which a check is performed as to whether further MR images should be generated. If this is not the case, the method finishes. By contrast, if further MR images should be generated, the method jumps back to step S2.

If quality inspections are defined for the utilized protocol (yes in step S3), the method according to an embodiment of the invention branches to step S4, in which the quality inspections defined for the method are performed.

A check is performed in the subsequent step S5 as to whether one of these quality inspections failed. If this is not the case (no in step S5) the method according to an embodiment of the invention branches to the previously described step S7.

If at least one of the quality inspections failed (yes in step S5) an action defined for the respective quality inspection in step S1 is automatically performed, depending on the failed quality inspection, for each failed quality inspection. As a result of this action the protocol is modified or another protocol is selected in order to improve the image quality of further MR images that are generated in step S2 with the aid of the modified or newly determined protocol. The method subsequently reaches the previously described step S7.

The quality inspections and actions (see step S1) can be configured by way of a table (see e.g. table 1 below), which is edited by the operator according to his/her ideas. This table firstly defines which quality inspections are performed and secondly defines what action is performed when one of these quality inspections fails.

The following table 1 shows, in an example fashion, the configuration in an MRI examination of the liver by way of MR images.

TABLE 1

Quality inspections and associated action

| Quality inspection | Action | Comment |
|---|---|---|
| The global signal-to-noise ratio is too small | Generate a warning and guide the operator when modifying or newly selecting the protocol. | The image quality is low and the operator should carefully inspect the MR images |
| The global signal-to-noise ratio is too small, and the inspection of the protocol failed | Guide the operator in modifying or newly selecting the protocol and select the correct reception coils | The signal-to-noise ratio is too small because the wrong reception coils were selected |
| A patient movement was registered | Select a protocol supporting an uncooperative strategy | The patient is uncooperative |
| The inspection of the protocol failed | Perform an automatic protocol optimization | The operator set wrong protocol parameters |
| There is insufficient fat saturation | Modify the strategy or parameters in respect of fat saturation | A wrong RF pulse sequence for fat saturation was utilized |

TABLE 1-continued

Quality inspections and associated action

| Quality inspection | Action | Comment |
|---|---|---|
| All other | Generate a warning | The operator should inspect the MR images |

A more precise definition of quality inspections in respect of an MRI examination of the liver by means of MR images could, for example, lead to the following quality inspections:
 The global signal-to-noise ratio must be greater than 2.
 The liver movement must not exceed 2 mm.
 The MR image quality must correspond to a quality of MR images generated for training purposes.
 The TE (echo time) protocol parameter must be smaller than 10 ms.

By contrast, the definition of quality inspections in respect of an MRI examination of the prostate by way of MR images could lead to the following quality inspections:
 The local signal-to-noise ratio (prostate to surrounding air) must be greater than 2.
 The MR image quality must correspond to a quality of MR images generated for training purposes.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for acquiring magnetic resonance (MR) images of a volume section within an examination object by way of a magnetic resonance scanner, the method comprising:
 acquiring at least one of the MR images;
 automatically performing a number of quality inspections on the at least one acquired MR image;
 automatically determining if an outcome of at least one of the number of quality inspection has failed; and
 automatically performing an action for improving image quality of at least one subsequent MR image to be acquired, if the determining determines that the outcome of at least one of the number of quality inspections has failed, the action performed being an action prescribed for the at least one of the number of quality inspections that has failed.

2. The method as claimed in claim 1, wherein the quality inspection is only performed in a region of the at least one MR image.

3. The method as claimed in claim 1, wherein the plurality of quality inspections are prescribed depending on a type of the volume section.

4. The method as claimed in claim 1, wherein the MR images are acquired depending on a protocol, and the quality inspections are determined automatically depending on the protocol.

5. The method as claimed in claim 1, wherein the quality inspections comprise at least one of:
inspecting whether a global signal-to-noise ratio of the at least one MR image lies above a first threshold,
inspecting whether a signal-to-noise ratio lies above a second threshold for a region within the volume section,
inspecting whether a registered movement of a region lies above a third threshold during the acquiring of the at least one MR image,
inspecting whether aliasing occurs within the at least one MR image to an extent that is above a fourth threshold,
inspecting whether a signal caused by fat has a value that lies above a fifth threshold,
comparing the at least one MR image with other MR images in order to inspect the quality of the at least one MR image depending on the comparison, and
inspecting whether setting parameters for acquiring the at least one MR image lie within defined ranges.

6. The method as claimed in claim 1, wherein the action includes performing at least one of:
at least one setting parameter for acquiring the at least one MR image is automatically modified, depending on the failed outcome of at least one of the number of quality inspections, such that a quality of the MR images that are to be acquired with the modified setting parameters is improved compared to a quality of the at least one MR image in which the outcome of at least one of the number of quality inspections failed,
a number of protocols from which one protocol is selectable by an operator is restricted such that the protocols of the restricted number improve a quality of those MR images that are produced by one of the protocols of this number compared to a quality of the at least one MR image in which the outcome of at least one of the number of quality inspections failed, and
a warning is generated for a user.

7. The method as claimed in claim 6, wherein, when the setting parameters are modified, the user is guided such that the change results in a quality of those MR images that are to be acquired with the modified setting parameters are improved over a quality of the at least one MR image in which the outcome of at least one of the number of quality inspections failed.

8. A magnetic resonance scanner for acquiring magnetic resonance (MR) images of a volume section in an examination object, the magnetic resonance scanner comprising:
a basic field magnet;
a gradient field system;
a radio frequency (RF) antenna; and
a control apparatus configured to,
actuate the gradient field system and the RF antenna,
acquire at least one MR image via the actuated gradient field system and the RF antenna,
perform a number of quality inspections in respect of the at least one acquired MR image,
determine if an outcome of at least one of the number of quality inspection has failed; and
perform an action to improve image quality of at least one subsequent MR image to be acquired, if the control apparatus determines that the outcome of at least one of the number of quality inspections has failed, the action performed being an action prescribed for the at least one of the number of duality inspections that has failed.

9. A non-transitory computer readable medium including a computer program product, the computer program product comprising program segments, which when executed on a computer device, causes the computer device to perform functions including:
acquiring at least one magnetic resonance (MR) image of a volume section within an examination object by way of a magnetic resonance scanner;
automatically performing a number of quality inspections on the at least one recorded MR image;
automatically determining if an outcome of at least one of the number of quality inspection has failed; and
automatically performing an action to improve image quality of at least one subsequent MR image to be acquired, if the determining determines that the outcome of at least one of the number of quality inspections has failed, the action performed being an action prescribed for the at least one of the number of quality inspections that has failed.

* * * * *